United States Patent

Socci et al.

| [11] | Patent Number: | 5,977,217 |
|---|---|---|
| [45] | Date of Patent: | Nov. 2, 1999 |

[54] QUICK DRYING NAIL ENAMEL COMPOSITION

[75] Inventors: Robert L. Socci, Cedar Grove, N.J.; Anatoly Ismailer, Roslyn Heights, N.Y.

[73] Assignee: Kirker Enterprises, Inc., Paterson, N.J.

[21] Appl. No.: 09/056,111

[22] Filed: Apr. 7, 1998

[51] Int. Cl.⁶ ........................................................ A61K 7/04
[52] U.S. Cl. ................................. 524/35; 424/61; 523/105
[58] Field of Search ................................. 524/35; 424/61; 523/105

[56] References Cited

U.S. PATENT DOCUMENTS

| 4,166,110 | 8/1979 | Isobe et al. . |
| 4,832,944 | 5/1989 | Socci et al. ................................. 424/61 |
| 5,045,309 | 9/1991 | Dell'Aquila . |
| 5,225,195 | 7/1993 | Soyama et al. . |
| 5,549,930 | 8/1996 | Reysis . |
| 5,561,174 | 10/1996 | Salto et al. . |
| 5,580,548 | 12/1996 | Mellul et al. . |
| 5,662,891 | 9/1997 | Martin . |
| 5,688,494 | 11/1997 | Graves et al. . |
| 5,804,169 | 9/1998 | Ramin . |
| 5,843,412 | 12/1998 | de La Poterie et al. . |

*Primary Examiner*—Nathan M. Nutter
*Attorney, Agent, or Firm*—Lerner, David, Littenberg, Krumholz & Mentlik, LLP

[57] ABSTRACT

A quick drying nail enamel composition using conventional solvents has improved scratch and mar resistance. The composition includes a polyether modified dimethylpolysiloxane where the polyether groups are polymers of ethylene oxide and propylene oxide.

42 Claims, No Drawings

QUICK DRYING NAIL ENAMEL COMPOSITION

FIELD OF THE INVENTION

The present invention relates in general to nail enamel compositions, and more particularly, to such compositions which in addition to being quick drying are suitable for use as color coats for coating natural and synthetic nails, as well as being suitable for use in single coat applications.

BACKGROUND OF THE INVENTION

Nail enamel compositions include a class of nail care products regularly used by women as part of their beauty care routine. These nail care products are available in a multitude of product formulations, from clears to infinite colors. Typically, clear nail enamel compositions include a primary film forming polymer, a secondary film forming resin, a plasticizer and one or more solvents. In the case of a color nail enamel composition, the product will also include a thixotropic compound as a suspending agent and one or more pigments, or in the alternative, an organic coloring polymer may be used. In addition to these components, a number of optional and proprietary components are often included such as UV light absorbers, moisturizers, stabilizers, fragrances and the like.

Despite the diverse formulation differences between known nail enamel compositions, the desirable performance expectations are frequently the same, for example, smooth application, rapid dry time, scratch and mar resistance, detergent and oil resistance, lustrous appearance and, often most importantly, wear and peel resistance. Of these expectations, rapid dry time has been considered particularly important to the user when applying nail enamel compositions. To this end, there are known a number of nail enamel compositions which claim to promote rapid dry times as a result of the use of specific components in the nail enamel composition.

By way of example, Pappas, et al., U.S. Pat. No. 5,206,011, discloses a nail enamel composition claimed to possess the property of rapid dry times by including acetone as a low boiling solvent. In Martin, U.S. Pat. No. 5,662,891, an acetone free nail enamel composition having rapid dry times is disclosed based upon the inclusion of a mixture of aliphatic and cycloaliphatic solvents. The nail enamel composition is suitable for use as a colorless base coat which prevents solvents being trapped between the base coat and an applied pigmented color coat of conventional composition. Martin also discloses the use of a smoothing agent to reduce friction to improve the flow of the nail enamel composition during application, resulting in improved levelness and surface gloss of the coating. Suitable smoothing agents include silicone polymers and copolymers, polyamides, polyacrylamides, polycarboxylic acids and mixtures thereof. One such polysiloxane copolymer is identified as a solution of a polyether modified dimethylpolysiloxane copolymer in ethylene glycol monobutyl ether.

In Dell'Aquila, U.S. Pat. No. 5,045,309, there is disclosed a nail enamel composition having rapid dry times based upon the inclusion of an accelerator compound in the nature of a fluorinated and/or chlorinated hydrocarbon. In Graves, et al., U.S. Pat. No. 5,688,494, a nail enamel composition having rapid dry times is based upon the use of a vinyl-silicone graft or block copolymer such as a silicone polymer segment and a vinyl polymer segment. In Soyama, et al., U.S. Pat. No. 5,225,195, there is disclosed the incorporation of a special silicone resin to provide a nail enamel composition possessing acceptable luster and durability, and rapid dry times. In Reysis, U.S. Pat. No. 5,549,930, there is disclosed a drying accelerator for a nail enamel composition which is a mixture of dimethicone and cyclomethicone which are applied to an underlying wet nail enamel coat. The drying accelerator extracts solvents from the wet nail enamel coat to achieve rapid dry times.

Notwithstanding these known nail enamel compositions, there is still the need for further improvements in nail enamel compositions which possess rapid dry times while retaining the other desirable performance expectations. Accordingly, the present invention broadly discloses nail enamel compositions having rapid dry times, scratch and mar resistance, detergent and oil resistance, lustrous appearance, wear and peel resistance, as well as being suitable for use in single color coat application.

SUMMARY OF THE INVENTION

A broad object of the present invention is to provide nail enamel compositions which are suitable for use as color coats, while maintaining the desirable characteristics of nail enamel compositions.

Another object of the present invention is to provide nail enamel compositions which retain their desirable characteristics while possessing rapid dry times.

Another object of the present invention is to provide nail enamel compositions which are quick drying, as well as being suitable for use in single color coat applications.

Another object of the present invention is to provide nail enamel compositions which are quick drying while having improved scratch and mar resistance.

In accordance with one embodiment of the present invention there is disclosed a quick drying color nail enamel composition comprising at least two film forming polymers, one of the film forming polymers comprising nitrocellulose, a film forming resin selected from the group consisting of epoxy resin, polyester resin and mixtures thereof, a plurality of cycloaliphatic free solvents, at least one of the solvents comprising ethyl acetate, a plasticizer selected from the group consisting of sucrose acetate isobutyrate, triphenyl phosphate, dibutyl phthalate and mixtures thereof, a suspending agent, polyether modified dimethylpolysiloxane and at least one pigment.

In accordance with another embodiment of the present invention there is disclosed a quick drying color nail enamel composition comprising at least two film forming polymers selected from the group consisting of nitrocellulose, ethyl cellulose, cellulose acetate butyrate, methacrylate and acrylate polymers and copolymers, and mixtures thereof, at least one of the film forming polymers comprising nitrocellulose, a film forming resin selected from the group consisting of tosylamide epoxy resin, polyester resin, toluene sulfonamide formaldehyde resin and mixtures thereof, a plurality of cycloaliphatic free solvents selected from the group consisting of ethyl acetate, butyl acetate, isopropyl alcohol, heptane, propyl acetate, diacetone alcohol and mixtures thereof, at least one of the solvents comprising ethyl acetate, a plasticizer selected from the group consisting of sucrose acetate isobutyrate, triphenyl phosphate, camphor, dibutyl phthalate and mixtures thereof, a suspending agent selected from the group consisting of stearalkonium hectorite, stearalkonium bentonite and mixtures thereof, polyether modified dimethylpolysiloxane and at least one pigment.

In accordance with another embodiment of the present invention there is disclosed a quick drying color nail enamel composition comprising a mixture of nitrocellulose and acrylates copolymer present in the range of about 11 to 25% by weight, a mixture of tosylamide epoxy resin and polyester resin present in the range of about 3 to 15% by weight, a mixture of ethyl acetate, butyl acetate, isopropyl alcohol, heptane, propyl acetate and diacetone alcohol present in the range of about 44 to 85% by weight, a mixture of sucrose acetate isobutyrate, triphenyl phosphate, camphor and dibutyl phthalate present in the range of about 4 to 20% by weight, polyether modified dimethylpolysiloxane present in the range of about 0.1 to 1.0% by weight of the composition, a suspending agent and at least one pigment.

In accordance with another embodiment of the present invention there is disclosed a quick drying color nail enamel composition comprising at least two film forming polymers, one of the film forming polymers comprising nitrocellulose, a film forming resin, a plurality of cycloaliphatic free solvents, a plasticizer, a suspending agent, a polyether modified dimethylpolysiloxane having a polyether group at either end and at least one pigment.

These and other objects, features and advantages of the present invention, as well as details of the preferred embodiments thereof, will be more further understood from the following detailed description.

DETAILED DESCRIPTION OF THE PREFERRED EMBODIMENTS

Quick drying nail enamel compositions of the present invention for coating a natural or synthetic nail broadly include the ingredients of a primary film forming polymer, a film forming resin, a plasticizer, an effective amount of a polyether modified dimethylpolysiloxane, a solvent, a thixotropic suspending agent and one or more pigments, or organic coloring polymers. In addition to the above components, the nail enamel compositions according the present invention may further include one or more additional ingredients, for example, UV light absorbers, stabilizer, fragrances, moisturizers, leveling agents, anti-foaming agents and the like. Nail enamel compositions of these components are useful in a wide variety of cosmetic applications such as color coats for single or multiple coat applications.

The nail enamel compositions of the present invention contain one or more primary film forming polymers, for example, cellulose acetate, cellulose acetate butyrate, ethyl cellulose, vinyl polymers, nitrocellulose, as well as methacrylate and acrylate type polymers and copolymers. The preferred primary film forming polymer for use in the present invention is nitrocellulose which provides an unusual combination of properties of toughness, durability, solubility and solvent release. Examples of nitrocellulose are the so called nitrocellulose RS ⅛ sec. and ¼ sec.; nitrocellulose ½ sec.; and nitrocellulose RS 5–6 sec. and 60–80 sec., which have higher viscosities than the earlier grades. The term "RS" refers to the brand of nitrocellulose with a nitrogen content of about 11.2–12.8% with solubility in esters, ketones and glycol ethers manufactured by Hercules, Inc. The terms ⅛ sec., ¼ sec., ¼ sec., 5–6 sec., etc. represent viscosity and refer to the time it takes for a ball to fall to a given depth in the material. Nitrocellulose is typically supplied in 70% concentrations, wet with 30% ethyl or isopropyl alcohol. As used in the present application, the percentage of nitrocellulose in a given composition will be on a dry basis, which range from about 10 to 20% by weight, and preferably in the range of about 12 to 16% by weight of the nail enamel composition.

In addition to the use of nitrocellulose as the primary film forming polymer, it is preferred that at least one additional film forming polymer be present. Preferably, the additional film forming polymer will be acrylate type polymers and copolymers present in an amount ranging from about 1 to 5% by weight of the nail enamel composition. The use of the second film forming polymer provides the properties of better adhesion of the nail enamel composition to the human nail and greater flexibility.

The use of too small an amount of nitrocellulose tends to result in the coated films being easily damaged. On the other hand, the use of too large an amount of nitrocellulose can result in the coated film being too hard and brittle, which easily causes undesirable peeling and hence poor wear resistance. Nail enamel compositions of the present invention include primary film forming polymers and combinations thereof in an amount ranging from about 11 to 25% by weight, and preferably in the range of about 13 to 21% by weight of the nail enamel composition.

In addition to the primary film forming polymer, the nail enamel compositions of the present invention may also include an amount of one or more film forming resins effective to strengthen the primary film forming polymer and to provide the nail enamel coating with acceptable gloss and adhesion characteristics. Exemplary secondary film forming resins which may be used in the present invention include, for example, drying and non-drying alkyd resins, polyvinyl resins for example polyvinyl acetate, polyester resins, acrylic polymers and copolymers, maleic modified glycerol esters of rosin and toluene sulfonamide/epoxy resins, e.g., tosylamide epoxy resin. It is also within the scope of nail enamel compositions of the present invention to include aldehyde condensation products such as arylsulfonamide formaldehyde resins, specifically toluene sulfonamide formaldehyde resin which is a condensation product of formaldehyde and toluene sulfonamide. These secondary film forming resins are added to the nail enamel compositions of the present invention to strengthen and add acceptable wear characteristics to the primary film forming polymer. The preferred film forming resins include tosylamide epoxy resin, polyester resin and mixtures thereof. In general, the amount of film forming resin and combinations thereof range from about 3 to 15% by weight of the composition, and preferably about 5 to 10% by weight of the nail enamel composition.

In addition to the primary film forming polymer and film forming resin, the nail enamel compositions according to the present invention also includes one or more plasticizers to soften and plasticize the primary film forming polymer. Suitable plasticizers for use in the nail enamel compositions include, for example, known plasticizers such as sucrose acetate isobutyrate, tricresyl phosphate, dibutyl tartrate, benzyl benzoate, 2, 2, 4-trimethyl-1, 3-pentanediol diisobutyrate, tributyl phosphate, butyl acetyl ricinoleate, butyl glycolate, butyl stearate, triphenyl phosphate, triethyl citrate, camphor, castor oil, esters of citric, stearate, phthalic, oleic, phosphate butyric and benzoic acid, glyceryl triacetate and glyceryl triproprionate and mixtures thereof, and phthalate type plasticizers, for example, diamylphthalate, dibutyl phthalate, diethyl phthalate, dioctyl phthalate, dibutoxy ethylphthalate and mixtures thereof.

Plasticizers included in the compositions of the present invention are in amounts sufficient to provide acceptable flexibility to the nail enamel film on the human or synthetic nail surface. In this regard, the amount of the plasticizers for use in the nail enamel compositions of the present invention range from about 4 to 20% by weight, and preferably about 6 to 10% by weight of the nail enamel composition.

The nail enamel compositions of the present invention include one or more solvents such as those generally used in conventional nail enamel compositions. Examples of these solvents include ethyl acetate, methyl acetate, ethanol, isopropanol, diacetone alcohol, propyl acetate, n-butanol, xylene, aromatic (containing phenyl groups), amyl acetate, ethers, ketones, toluene alkanes for example, pentane, cyclopentane, hexane, heptane, cyclohexane, cyclic ethers for example, tetrahydrofuran and 1,4-dioxane, cellosolve, butyl cellosolve acetate, cellosolve acetate, methyl cellosolve acetate, butyl cellosolve, ethyl cellosolve, phenylated solvents for example, xylene, esters of acetic acid for example, methyl acetate, ethyl acetate, n-butyl acetate, chlorinated hydrocarbons for example, methylene chloride, chloroform and methylchloroform. The aforementioned solvents can be used alone or in mixtures thereof. In general, the amount of solvent used in the compositions of the present invention range from about 44 to 85% by weight, and preferably from about 50 to 75% by weight of the nail enamel composition.

The nail enamel composition of the present invention includes a polyether modified dimethylpolysiloxane of the formula:

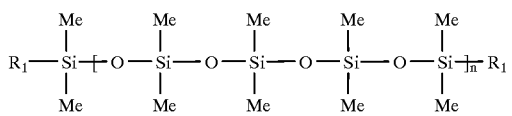

Wherein $R_1$ is a polyether group, and specifically, a polymer of ethylene oxide with propylene oxide known as an EUPO polymer. The polymer composition has a number average molecular weight of about 4800. The described polyether modified dimethylpolysiloxane is commercially available from BKY-Chemie, USA of Wallingford, Connecticut under the trademark BKY-333. It has been found that when adding an effective amount of the polyether modified dimethylpolysiloxane identified as BKY-333 to a nail enamel composition, the resulting composition exhibited increased resistance to surface marring over nail enamel compositions formulated without the presence of the polyether modified dimethylpolysiloxane, while exhibiting quick drying properties. By way of example, the polyether modified dimethylpolysiloxane may be included in an amount ranging from about 0.1 to 1% by weight, preferably in the range of from about 0.3 to 0.6% by weight, and most preferably about 0.40% by weight of the nail enamel composition.

In the color compositions according to the present invention, one or more pigments and a thixotropic agent are also added. One or more known organic colorants may also be added to these compositions. Pigments are added to the composition to provide cosmetically acceptable shades and to pacify the films. Pigments for use in the present invention may include any of those pigments which are generally known for use in nail enamel compositions. For example, these pigments can include cosmetic grade or purified titanium dioxide, yellow and red iron oxides, bismuth oxychloride, iron blue, iron black, mica particles, ultramarine blue, D&C Red #7, chromide oxide greens, carbon black and lampblack. Other pigments which may be used in compositions according to the present invention may include the Lake pigments, for example, D&C Red #6 barium Lake and D&C Red #7 calcium Lake.

In addition to the above named pigments, there may also be included titanated micas, polyethylene teraphthalates and pearl essence which is a suspension of crystalline guanine in nitrocellulose and solvents, as well as other additives which will affect the appearance of the pigment. Although the amount of pigment in the compositions of the present invention will vary as a function of the type of pigment and other components included in the composition, in general, pigments can be included in an amount up to about 10% by weight of the nail enamel composition.

When pigments are included in compositions according to the present invention, it is useful to include a thixotropic agent for enhancing the suspension of the pigments in the other components of the composition. Although a number of thixotropic agents which are generally used in conventional nail enamel compositions may be used to produce compositions according to the present invention, preferred thixotropic agents include the thixotropic clays, especially stearalkonium hectorite, stearalkonium bentonite and mixtures thereof. The thixotropic agent is present in the compositions of the present invention in amounts sufficient to produce a gel, preferably a colloidal gel. In general, the thixotropic agent is included in the amount ranging from about 0.5 to 5% by weight of the nail enamel composition.

There are known a number of anti-foaming agents which are suitable for use in nail enamel compositions which also function as leveling agents. Examples of satisfactory anti-foaming and/or leveling agents include dimethicone available from Dow Corning, Chemical Products Division in Midland, Mich., identified as Dow Corning 200; nonionic acetylenic diol surfactant available from Air Products and Chemicals, Inc. of Allentown, Pa. under the mark Surfynol 104 Surfactant and the ethoxylated analogs under the marks Surfynol 440, 465 and 485 surfactants, and Surfynol DF-110 defoamer series; as well as a number of foam destroying silicon free polymers, polysiloxanes, polysiloxane copolymers and mixtures thereof available from BKY-Chemie, USA of Wallingford, Connecticut under the marks BKY-052 (silicon free), BKY-053 (silicon free), BKY-065, BKY-070 and BKY-80. The preferred anti-foaming agent for use in accordance with the present invention is dimethicone.

In general, the anti-foaming agent is included in an effective amount to inhibit bubbling of the nail enamel composition during the drying process. By way of example, the anti-foaming agent may be included in an amount ranging from about 0.05 to 0.5% by weight of the nail enamel composition.

In addition to the above described components, the compositions of the present invention may also include additional additives including stabilizers, UV light absorbers such as ectocrylene and benzophenone-1, fragrances, moisturizers and medicants, depending on the intended result. These components are well known in the art and may be included in amounts well within the teachings of the prior art.

The nail enamel compositions in accordance with the present invention can be manufactured by thoroughly and intimately mixing together all the components in the amounts described in accordance with the present invention. Examples of satisfactory equipment and how to use then are readily apparent to one of ordinary skill in the nail enamel art.

The following example illustrates a nail enamel composition of the present invention including the combination of preferred components and the approximate range that each component may be included in the disclosed formulation in accordance with one embodiment of the present invention. This example is by way of illustration and is not intended to be limiting the present invention either as to the inclusion of a lesser number of components, the substitution of additional components or variations in the percentages of the range of components.

EXAMPLE 1

| INGREDIENTS | WT/% RANGE |
|---|---|
| ETHYL ACETATE | 30.0–50.00 |
| BUTYL ACETATE | 10.0–20.00 |
| NITROCELLULOSE | 10.0–20.00 |
| ISOPROPYL ALCOHOL | 4.00–10.00 |
| TOSYLAMIDE EPOXY RESIN | 3.00–10.00 |
| SUCROSE ACETATE ISOBUTYRATE | 3.00–10.00 |
| ACRYLATES COPOLYMER | 1.00–5.00 |
| TRIPHENYL PHOSPHATE | 1.00–5.00 |
| POLYESTER RESIN | 0.50–2.00 |
| DIBUTYL PHTHALATE | 0.10–2.00 |
| CAMPHOR | 0.05–1.50 |
| HEPTANE | 0.05–1.50 |
| PROPYL ACETATE | 0.50–2.00 |
| STEARALKONIUM HECTORITE | 0.75–2.00 |
| STEARALKONIUM BENTONITE | 0.05–2.00 |
| DIACETONE ALCOHOL | 0.25–1.00 |
| BENZOPHENONE 1 | 0.05–0.50 |
| POLYETHER MODIFIED DIMETHYLPOLYSILOXIANE | 0.20–1.00 |
| ETOCRYLENE | 0.05–1.50 |
| DIMETHICONE | 0.05–0.50 |
| PIGMENT | 0.50–10.00 |

The following specific examples are provided to illustrate the nail enamel compositions of the present invention and should not be construed to limit the scope of the invention in any way.

EXAMPLE 2

| INGREDIENTS | WT/PERCENT |
|---|---|
| ETHYL ACETATE | 43.60 |
| BUTYL ACETATE | 12.40 |
| NITROCELLULOSE | 12.00 |
| ISOPROPYL ALCOHOL | 5.50 |
| TOSYLAMIDE EPOXY RESIN | 6.50 |
| SUCROSE ACETATE ISOBUTYRATE | 5.00 |
| R779 ACRYLATES COPOLYMER | 3.75 |
| TRIPHENYL PHOSPHATE | 3.75 |
| POLYESTER RESIN | 0.75 |
| DIBUTYL PHTHALATE | 0.50 |
| DIACETONE ALCOHOL | 0.50 |
| BENZOPHENONE 1 | 0.10 |
| POLYETHER MODIFIED DIMETHYLPOLYSILOXANE | 0.50 |
| DIMETHICONE | 0.20 |
| STEARALKONIUM HECTORITE | 1.00 |
| TITANIUM DIOXIDE | 1.00 |
| D&C RED #6 CALCIUM LAKE | .75 |
| RED IRON OXIDE | 1.00 |
| BLACK IRON OXIDE | .20 |
| MICA | 1.00 |

EXAMPLE 3

| INGREDIENTS | WT/PERCENT |
|---|---|
| ETHYL ACETATE | 37.01 |
| BUTYL ACETATE | 14.20 |
| NITROCELLULOSE | 12.80 |
| ISOPROPYL ALCOHOL | 6.40 |
| TOSYLAMIDE EPOXY RESIN | 6.60 |
| SUCROSE ACETATE ISOBUTYRATE | 5.90 |
| ACRYLATES COPOLYMER | 0.70 |
| TRIPHENYL PHOSPHATE | 2.70 |
| POLYESTER RESIN | 1.20 |
| DIBUTYL PHTHALATE | 0.90 |
| CAMPHOR | 0.10 |
| HEPTANE | 0.30 |
| PROPYL ACETATE | 0.20 |
| STEARALKONIUM HECTORITE | 0.10 |
| STEARALKONIUM BENTONITE | 1.10 |
| DIACETONE ALCOHOL | 0.70 |
| BENZOPHENONE 1 | 0.30 |
| POLYETHER MODIFIED DIMETHYLPOLYSILOXANE | 0.40 |
| ETOCRYLENE | 0.05 |
| DIMETHICONE | 0.10 |
| TITANIUM DIOXIDE | 0.20 |
| FD&C YELLOW #5 ALUMINUM LAKE | 1.00 |
| FERRIC AMMONIUM FERROCYANIDE | 0.04 |
| MICA | 7.00 |

EXAMPLE 4

| INGREDIENTS | WT/PERCENT |
|---|---|
| ETHYL ACETATE | 41.20 |
| BUTYL ACETATE | 15.80 |
| NITROCELLULOSE | 11.50 |
| ISOPROPYL ALCOHOL | 6.40 |
| TOSYLAMIDE EPOXY RESIN | 6.60 |
| SUCROSE ACETATE ISOBUTYRATE | 5.90 |
| ACRYLATES COPOLYMER | 0.70 |
| TRIPHENYL PHOSPHATE | 2.90 |
| POLYESTER RESIN | 0.60 |
| DIBUTYL PHTHALATE | 1.70 |
| CAMPHOR | 0.20 |
| HEPTANE | 0.50 |
| PROPYL ACETATE | 0.50 |
| STEARALKONIUM HECTORITE | 0.10 |
| STEARALKONIUM BENTONITE | 0.80 |
| DIACETONE ALCOHOL | 0.50 |
| BENZOPHENONE 1 | 0.05 |
| POLYETHER MODIFIED DIMETHYL POLYSILOXANE | 0.40 |
| ETOCRYLENE | 0.05 |
| DIMETHICONE | 0.10 |
| TITANIUM DIOXIDE | 2.00 |
| FD&C YELLOW #5 ALUMINUM LAKE | 0.10 |
| RED IRON OXIDE | 0.10 |
| BLACK IRON OXIDE | 1.30 |

One object of the present invention is to provide a nail enamel composition containing conventional solvents which dries in less than about 90 seconds when brushed on the nail. The nail enamel compositions of Examples 3 and 4 were tested for drying times. One coat of a nail enamel composition of each example, respectively, was brushed onto a human nail depositing a color film. The test film was lightly touched with the tip of a clean finger and the finger tip was immediately placed against a piece of clear, clean glass to determine when the film did not adhere to the finger or transfer to the glass. When there was no transfer, the nail enamel coating was considered "set-to-touch." The standard environment used for determining the dry time for air drying the coating was a temperature of $73.4°±3.6°$ F. and a relative humidity of $50°±5\%$. The nail enamel coating of Example 3 exhibited a set-to-touch time of 60 seconds and the Example 4 nail enamel coating exhibited a set-to-touch time of 80 seconds.

Although the invention herein has been described with reference to particular embodiments, it is to be understood that the embodiments are merely illustrative of the principles and application of the present invention. It is therefore to be understood that numerous modifications may be made to the embodiments and that other arrangements may be devised without departing from the spirit and scope of the present invention as defined by the claims.

What is claimed is:

1. A quick drying color nail enamel composition comprising at least two film forming polymers, one of said film forming polymers comprising nitrocellulose, a film forming resin selected from the group consisting of epoxy resin, polyester resin and mixtures thereof, at least two cycloalphatic free solvents, at least one of said solvents comprising ethyl acetate, a plasticizer selected from the group consisting of sucrose acetate isobutyrate, triphenyl phosphate, dibutyl phthalate and mixtures thereof, at least one pigment, a suspending agent and polyether modified dimethylpolysiloxane present in said composition independent of said pigment in an effective amount to decrease the drying time of said composition.

2. The quick drying nail enamel composition of claim 1, wherein the other of said film forming polymers is selected from the group consisting of ethyl cellulose, cellulose acetate butyrate, methacrylate and acrylate polymers and copolymers, and mixtures thereof.

3. The quick drying nail enamel composition of claim 1, wherein said film forming resin further includes toluene sulfonamide formaldehyde resin.

4. The quick drying nail enamel composition of claim 1, wherein said solvents are selected from the group consisting of butyl acetate, isopropyl alcohol, heptane, propyl acetate, diacetone alcohol and mixtures thereof.

5. The quick drying nail enamel composition of claim 1, wherein said suspending agent is selected from the group consisting of stearalkonium hectorite, stearalkonium bentonite and mixtures thereof.

6. The quick drying nail enamel composition of claim 1, wherein said polyether modified dimethylpolysiloxane comprises dimethylpolysiloxane having a polyether group at either end, each said polyether group comprising a polymer of ethylene oxide and propylene oxide.

7. The quick drying nail enamel composition of claim 1, further including an anti-foaming agent comprising dimethicone.

8. The quick drying nail enamel composition of claim 1, wherein said film forming polymers are present in the range of about 11 to 25% by weight, said film forming resin is present in the range of about 3 to 15% by weight, said solvents are present in the range of about 44 to 85% by weight, said plasticizer is present in the range of about 4 to 20% by weight and said polyether modified dimethylpolysiloxane is present in the range of about 0.1 to 1% by weight of said composition.

9. The quick drying nail enamel composition of claim 1, wherein said epoxy resin comprises tosylamide epoxy resin.

10. A quick drying color nail enamel composition comprising at least two film forming polymers selected from the group consisting of nitrocellulose, ethyl cellulose, cellulose acetate butyrate, methacrylate and acrylate polymers and copolymers, and mixtures thereof, at least one of said film forming polymers comprising nitrocellulose, a film forming resin selected from the group consisting of tosylamide epoxy resin, polyester resin, toluene sulfonamide formaldehyde resin and mixtures thereof, at least two cycloaliphatic free solvents selected from the group consisting of ethyl acetate, butyl acetate, isopropyl alcohol, heptane, propyl acetate, diacetone alcohol and mixtures thereof, at least one of said solvents comprising ethyl acetate, a plasticizer selected from the group consisting of sucrose acetate isobutyrate, triphenyl phosphate, camphor, dibutyl phthalate and mixtures thereof, at least one pigment, a suspending agent selected from the group consisting of stearalkonium hectorite, stearalkonium bentonite and mixtures thereof, and polyether modified dimethylpolysiloxane present in said composition independent of said pigment in an effective amount to decrease the drying time of said composition.

11. The quick drying nail enamel composition of claim 10, wherein said film forming polymers are present in the range of about 11 to 25% by weight, said film forming resin is present in the range of about 3 to 15% by weight, said solvents are present in the range of about 44 to 85% by weight, said plasticizer is present in the range of about 4 to 20% by weight, said polyether modified dimethylpolysiloxane is present in the range of about 0.1 to 1% by weight, and said suspending agent present in the range of about 0.5 to 4% by weight.

12. The quick drying nail enamel composition of claim 10, further including a UV absorber comprising a mixture of benzophenone-1 and etocrylene.

13. The quick drying nail enamel composition of claim 10, wherein said polyether modified dimethylpolysiloxane comprises dimethylpolysiloxane having a polyether group at either end, each said polyether group comprising a polymer of ethylene oxide and propylene oxide.

14. The quick drying nail enamel composition of claim 10, wherein said film forming polymers comprise a mixture of nitrocellulose and an acrylate copolymer.

15. The quick drying nail enamel composition of claim 10, wherein said film forming resin comprises a mixture of tosylamide epoxy resin and polyester resin.

16. The quick drying nail enamel composition of claim 10, wherein said solvents comprise a mixture of ethyl acetate, butyl acetate, isopropyl alcohol, heptane, propyl acetate and diacetone alcohol.

17. The quick drying nail enamel composition of claim 10, wherein said plasticizer comprises a mixture of sucrose acetate isobutyrate, triphenyl phosphate, camphor and dibutyl phthalate.

18. A quick drying color nail enamel composition comprising nitrocellulose and at least one acrylate copolymer present in the combined range of about 11 to 25% by weight, a mixture of tosylamide epoxy resin and polyester resin present in the range of about 3 to 15% by weight, a mixture of ethyl acetate, butyl acetate, isopropyl alcohol, heptane, propyl acetate and diacetone alcohol present in the range of about 44 to 85% by weight, a mixture of sucrose acetate isobutyrate, triphenyl phosphate, camphor and dibutyl phthalate present in the range of about 4 to 20% by weight, at least one pigment, polyether modified dimethylpolysiloxane present in said composition independent of said pigment in the range of about 0.1 to 1.0% by weight of said composition to decrease the drying time of said composition, and a suspending agent.

19. The quick drying nail enamel composition of claim 18, further including a UV absorber comprising a mixture of benzophenone-1 and etocrylene.

20. The quick drying nail enamel composition of claim 18, wherein said polyether modified dimethylpolysiloxane comprises dimethylpolysiloxane having a polyether group at either end, each said polyether group comprising a polymer of ethylene oxide and propylene oxide.

21. A quick drying color nail enamel composition comprising at least two film forming polymers, one of said film forming polymers comprising nitrocellulose, a film forming resin, at least two cycloaliphatic free solvents, a plasticizer, a suspending agent, at least one pigment, and a polyether modified dimethylpolysiloxane having a polyether group at either end present in said composition independent of said pigment in an effective amount to decrease the drying time of said composition.

22. The quick drying nail enamel composition of claim 21, wherein the other of said film forming polymers is selected from the group consisting of ethyl cellulose, cellulose acetate butyrate, methacrylate and acrylate polymers and copolymers, and mixtures thereof.

23. The quick drying nail enamel composition of claim 21, wherein said solvents are selected from the group consisting of ethyl acetate, butyl acetate, isopropyl alcohol, heptane, propyl acetate, diacetone alcohol and mixtures thereof.

24. The quick drying nail enamel composition of claim 21, wherein said film forming polymers are present in the range of about 11 to 25% by weight, said film forming resin is present in the range of about 3 to 15% by weight, said solvents are present in the range of about 44 to 85% by weight, said plasticizer is present in the range of about 4 to 20% by weight and said polyether modified dimethylpolysiloxane is present in the range of about 0.1 to 1 by weight of said composition.

25. The quick drying nail enamel composition of claim 21, wherein said polyether group comprises a polymer of ethylene oxide and propylene oxide.

26. A quick drying nail enamel composition comprising a primary film forming polymer, a film forming resin, at least one cycloaliphatic free solvent, a plasiticizer and a polyether modified dimethylpolysiloxane having the formula:

$$R_1-\underset{Me}{\overset{Me}{Si}}\!\!+\!\!O-\underset{Me}{\overset{Me}{Si}}-O-\underset{Me}{\overset{Me}{Si}}-O-\underset{Me}{\overset{Me}{Si}}-O-\underset{Me}{\overset{Me}{Si}}\!\!\tfrac{}{\ \!n}\!R_1$$

Wherein $R_1$ is a polyether group comprising a polymer of ethylene oxide and propylene oxide; said polyether modified dimethylpolysiloxane present in an effective amount to decrease the drying time of said composition.

27. The quick drying nail enamel composition of claim 26, wherein said polyether modified dimethylpolysiloxane has a number average molecular weight of about 4800.

28. The quick drying nail enamel composition of claim 26, wherein said polyether modified dimethylpolysiloxane is present in the range of about 0.1 to about 1% by weight of said composition.

29. The quick drying nail enamel composition of claim 26, further including a suspending agent and at least one pigment.

30. The quick drying nail enamel composition of claim 26, wherein said primary film forming polymer is selected from the group consisting of nitrocellulose, ethyl cellulose, cellulose acetate butyrate, methacrylate and acrylate polymers and copolymers, and mixtures thereof.

31. The quick drying nail enamel composition of claim 26, wherein said film forming resin is selected from the group consisting of epoxy resins, polyester resins, sulfonamide formaldehyde resins and mixtures thereof.

32. The quick drying nail enamel composition of claim 31, wherein said film forming resin comprises tosylamide epoxy resin.

33. The quick drying nail enamel composition of claim 32, wherein said film forming resin further includes a polyester resin.

34. The quick drying nail enamel composition of claim 26, wherein said primary film forming polymer comprises nitrocellulose and an acrylate copolymer.

35. The quick drying nail enamel composition of claim 1, wherein said polyether modified dimethylpolysiloxane comprises:

$$R_1-\underset{Me}{\overset{Me}{Si}}\!\!+\!\!O-\underset{Me}{\overset{Me}{Si}}-O-\underset{Me}{\overset{Me}{Si}}-O-\underset{Me}{\overset{Me}{Si}}-O-\underset{Me}{\overset{Me}{Si}}\!\!\tfrac{}{\ \!n}\!R_1$$

Wherein $R_1$ is a polyether group comprising a polymer of ethylene oxide and propylene oxide.

36. The quick drying nail enamel composition of claim 10, wherein said polyether modified dimethylpolysiloxane comprises:

$$R_1-\underset{Me}{\overset{Me}{Si}}\!\!+\!\!O-\underset{Me}{\overset{Me}{Si}}-O-\underset{Me}{\overset{Me}{Si}}-O-\underset{Me}{\overset{Me}{Si}}-O-\underset{Me}{\overset{Me}{Si}}\!\!\tfrac{}{\ \!n}\!R_1$$

Wherein $R_1$ is a polyether group comprising a polymer of ethylene oxide and propylene oxide.

37. The quick drying nail enamel composition of claim 18, wherein said polyether modified dimethylpolysiloxane comprises:

$$R_1-\underset{Me}{\overset{Me}{Si}}\!\!+\!\!O-\underset{Me}{\overset{Me}{Si}}-O-\underset{Me}{\overset{Me}{Si}}-O-\underset{Me}{\overset{Me}{Si}}-O-\underset{Me}{\overset{Me}{Si}}\!\!\tfrac{}{\ \!n}\!R_1$$

Wherein $R_1$ is a polyether group comprising a polymer of ethylene oxide and propylene oxide.

38. The quick drying nail enamel composition of claim 21, wherein said polyether modified dimethylpolysiloxane comprises:

$$R_1-\underset{Me}{\overset{Me}{Si}}\!\!+\!\!O-\underset{Me}{\overset{Me}{Si}}-O-\underset{Me}{\overset{Me}{Si}}-O-\underset{Me}{\overset{Me}{Si}}-O-\underset{Me}{\overset{Me}{Si}}\!\!\tfrac{}{\ \!n}\!R_1$$

Wherein $R_1$ is a polyether group comprising a polymer of ethylene oxide and propylene oxide.

39. The quick drying nail enamel composition of claim 35, wherein said polyether modified dimethylpolysiloxane has a number average molecular weight of about 4800.

40. The quick drying nail enamel composition of claim 36, wherein said polyether modified dimethylpolysiloxane has a number average molecular weight of about 4800.

41. The quick drying nail enamel composition of claim 37, wherein said polyether modified dimethylpolysiloxane has a number average molecular weight of about 4800.

42. The quick drying nail enamel composition of claim 38, wherein said polyether modified dimethylpolysiloxane has a number average molecular weight of about 4800.

* * * * *